United States Patent [19]
Goodman

[11] Patent Number: 5,200,146
[45] Date of Patent: Apr. 6, 1993

[54] APPARATUS FOR EFFECTING PLASMA STERILIZATION

[75] Inventor: Claude A. Goodman, Gaithersburg, Md.

[73] Assignee: Air Techniques, Inc., Hicksville, N.Y.

[21] Appl. No.: 661,553

[22] Filed: Feb. 26, 1991

[51] Int. Cl.⁵ .............................................. A61L 2/14
[52] U.S. Cl. ........................................ 422/23; 422/21; 422/22; 422/28; 422/292; 422/295; 422/297
[58] Field of Search ................ 422/21, 22, 23, 28, 422/292, 295, 297

[56] References Cited
U.S. PATENT DOCUMENTS

| | | | |
|---|---|---|---|
| 4,207,286 | 6/1980 | Boucher | 422/21 |
| 4,756,882 | 7/1988 | Jacobs et al. | 422/23 |
| 4,917,586 | 4/1990 | Jacob | 422/21 |
| 4,919,659 | 4/1990 | Horbett et al. | 435/285 |
| 4,931,261 | 6/1990 | Jacob | 422/292 |
| 4,976,920 | 12/1990 | Jacob | 422/23 |

Primary Examiner—Robert J. Warden
Assistant Examiner—Amalia Santiago
Attorney, Agent, or Firm—Louis E. Marn

[57] ABSTRACT

There is disclosed an invention for effecting sterilization in a plasma of low molecular weight aliphatic alcohol, preferably methanol at pressure levels of from 10 mTorr to 10 Torr at RF energy levels to establish and maintain a plasma for a time sufficient to achieve substantial total microbicidal effectiveness.

8 Claims, 3 Drawing Sheets

APPARATUS FOR EFFECTING PLASMA STERILIZATION

BACKGROUND OF THE INVENTION

1) Field of the Invention

This invention relates to sterilization, and more particularly to a process and apparatus for effecting plasma sterilization using low molecular weight aliphatic alcohols, preferably methanol.

2) Description of the Prior Art

There is a growing concern about the spread of infections during routine healthcare treatments due to public awareness of transmissible diseases including hepatitis and AIDS, also echoed by the CDC (Center for Disease Control) and the FDA (Food and Drug Administration) currently focused on nosocomial infection. A plethora of sterilization techniques are and have been practiced for years using heat, sterilization agents and the like, as well as including the use of plasma sterilization techniques. For instance in U.S. Pat. No. 3,383,163, there is disclosed the use of an argon RF plasma to sterilize the interior walls of glass bottles. A chemically reactive halogen gas RF plasma is disclosed in U.S. Pat. No. 3,701,628 to achieve sterilization at lower temperatures and while suitable for glass and plastic bottles, such method is corrosive to metals.

In U.S. Pat. No. 4,207,286, there is disclosed a method for passing an aldehyde feed gas RF plasma over objects to achieve surface sterilization. In U.S. Pat. No. 4,348,357, there is disclosed the use of pressure/power cycles to convectively force the (oxygen) RF plasma species into holes, apertures and cavitites as well as to sterilize objects of irregular shape. In U.S. Pat. No. 4,599,216, there is disclosed an apparatus for increasing the uniformity of microwave exposure by rotating dental items through the microwave field. A microwave adsorber is necessary to reduce the likelihood of metal objects arcing back to the magnetron, however, long exposures obtained erratic results—insufficient to justify claims of sterility.

In U.S. Pat. No. 4,643,876, there is disclosed the use of hydrogen peroxide (liquid) in the pre-treatment cycle and (vapor) as a precursor for active species made in an RF plasma. In U.S. Pat. No. 4,756,882 there is described the conversion of residual hydrogen peroxide into non-toxic decomposition products In U.S. Pat. No. 4,801,427 there is disclosed the use of hydrogen, oxygen, nitrogen, halogens, organohalogens, inorganic halogens, inorganic oxyhalogenated compounds, inert gases and mixtures to produce RF plasmas to sterilize medical instruments. In U.S. Pat. No. 4,804,431, there is described the modification of a conventional microwave oven to produce oxygen or argon plasmas for etching and cleaning.

Traditional sterilization methods include: ethylene oxide gas which leaves toxic residues; dry heat which may corrode metal; steam autoclaving dulling blades and points; chemical vapor (e.g. formaldehyde and gluteraldehyde); gamma, x-ray and electron beam/curtain radiation which is only suitable for batch or production line processing, etc. While all such techniques have achieved satisfactory levels of sterilization for particular uses of the thus sterilized item, such techniques suffer from universality to the materials of construction of items to be sterilized as well as requirements to store dangerous chemical sterilants with concomitant handling difficulties. Additionally, such techniques are ineffective in situations requiring rapid sterilization, e.g. in a surgical procedure when a critical instrument is unsterile, dropped or otherwise contaminated.

OBJECTS OF THE INVENTION

An object of the present invention is to provide a plasma sterilization process and apparatus of improved effectiveness.

Another object of the present invention is to provide a plasma sterilization process and apparatus eliminating the storage and handling of dangerous chemical sterilant agents.

A further object of the present invention is to provide a plasma sterilization process and apparatus of universality of application to articles being sterilized.

Still another object of the present invention is to provide a plasma sterilization process and apparatus of improved effectiveness for the rapid sterilization of critical items during surgical protocol.

Yet another object of the present invention is to provide a plasma sterilization process and apparatus not adversely affecting the physical or chemical properties of articles being decontaminated.

SUMMARY OF THE INVENTION

These and other objects of the present invention are achieved by a process and apparatus for effecting plasma sterilization using a low molecular weight aliphatic alcohol, preferably methanol, at pressure levels of from 10 mTorr to 10 Torr at RF energy levels to establish and maintain a plasma for a time sufficient to achieve substantially total microbicidal effectiveness.

BRIEF DESCRIPTION OF THE DRAWINGS

Further objects and advantages of the present invention will become more apparent from the following detailed description thereof when taken with the accompanying drawings wherein.

DETAILED DESCRIPTION OF THE INVENTION

Figure 1:
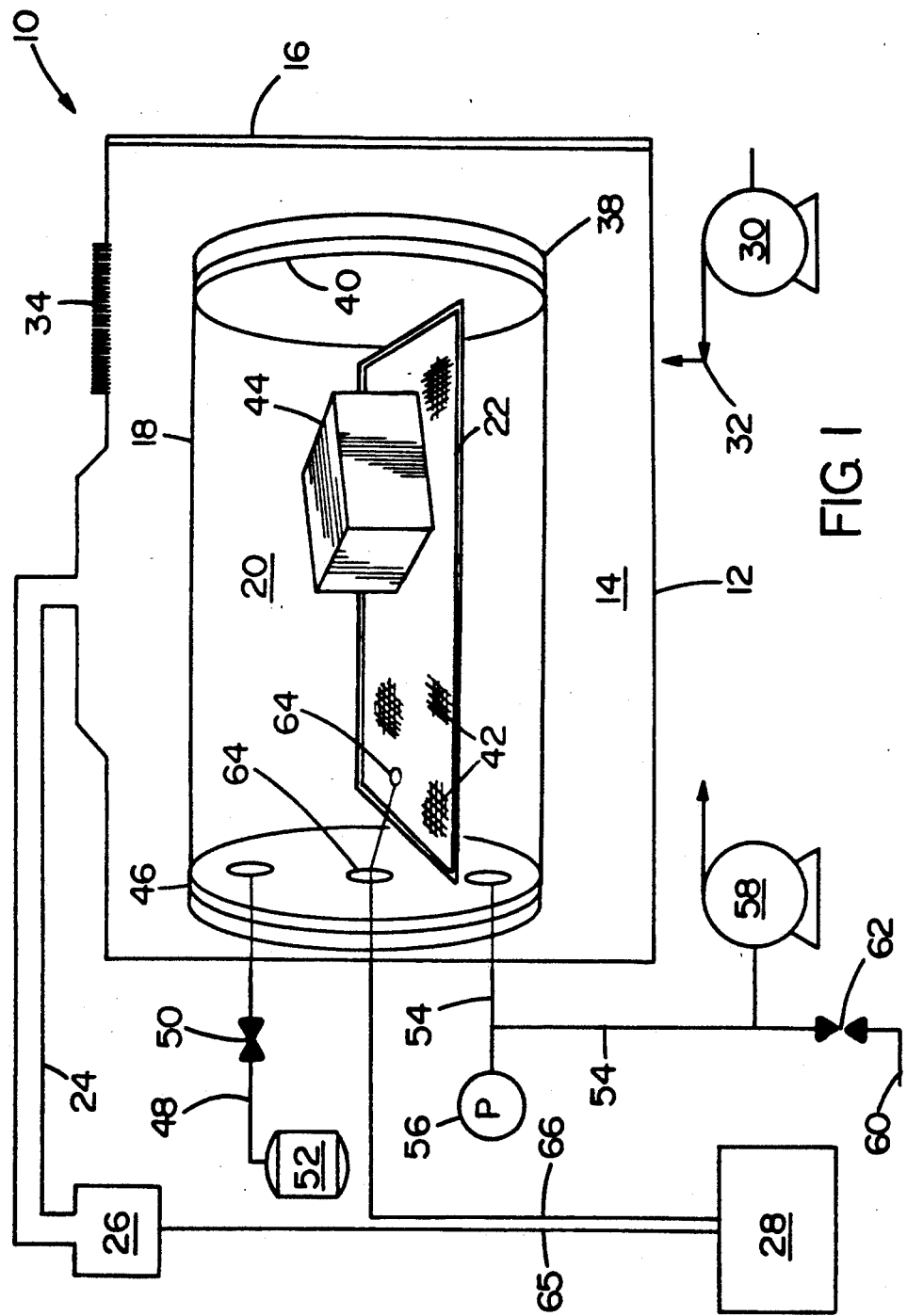
FIG. 1 is a schematic drawing of the apparatus of the present invention.

Referring now to FIG. 1, there is illustrated a plasma sterilization assembly, generally indicated as 10, comprised of a multimode reflective cavity or microwave oven 12 defining a microwave chamber 14 and including a door member 16. A horizontally-disposed cylindrically-shaped vessel 18 defining a sterilization chamber 20 is positioned within the microwave chamber 14 and is provided with a horizontally-disposed inert tray member 22 positioned therein. The microwave oven 12 is provided with a wave guide member 24 electromagnetically coupled to a source 26 of RF energy as known to one skilled in the art, connected to an electrical power supply (not shown) and modulated via a control panel 28 via conductor 65. The microwave oven 12 of the sterilizing assembly 10 is provided with a cooling fan 30 in fluid communication by a conduit 32 with the chamber 14 of the microwave oven 12 including a vent conduit 34 as more fully hereinafter discussed.

The vessel 18 is formed of a highly radiation-transparent material, such as quartz, Pyrex® glass or the like. The vessel 18 is provided with a cooperating cover member 38 including appropriate gasket member 40 to permit evacuation of the sterilization chamber 20 to below atmospheric pressure levels or a vacuum of from 10 mTorr to about 10 Torr. The cover member 38 is formed of an inert material, such as aluminum and is of a thickness sufficient to support the hereinabove disclosed below atmospheric pressure levels or vacuum. The tray member 22 is likewise formed of an inert material, such as aluminum, and is formed with a plurality of orifices 42 to permit effective plasma formation about the article (not shown) being sterilized. The dimensions of the tray member 22 are sized to be compatible with the wave form of the generated RF energy as more fully hereinafter discussed. An electrically conductive shield or Faraday cage 44, as known to one skilled in the art, may optionally be employed in the process and apparatus of the present invention.

A closed end 46 of the vessel 18 within the microwave oven 12 is provided with a conduit 48 under the control of valve 50 in fluid flow relationship to a storage vessel 52 for the aliphatic hydrocarbon alcohols, preferably methanol, and a conduit 54 including a vacuum pressure gauge 56 in fluid flow relationship with the suction side of a vacuum pump 58. The conduit 54 is in fluid flow relationship with the atmosphere via a conduit 60 under the control of a valve 62. Electronic sensor elements 64 are positioned within the vessel 18 and connected via conductor 66 to the control panel 28 including monitoring, energizing and process control members (not shown).

In operation, an article (not shown) to be sterilized is preferably first treated to remove gross detritus and possibly even subjected to ultrasonic cleaning techniques. The thus cleaned article is dipped into a low molecular weight aliphatic alcohol having 6 or less carbon atoms, and preferably methanol, as more fully hereinafter discussed. The article is then placed on the perforated tray 22 within the chamber 20 of the sterilization vessel 18. The door or cover 38 is positioned over the opening of the chamber 20 to thereby enclose the microwave oven 12. The door member 16 of the microwave oven 12 is thereafter closed thereby deactivating any upset switch permitting further operation of the apparatus of the present invention.

The cooling fan 30 is thus activated followed by activation of the vacuum pump 58 is activated to reduce pressure within the chamber 20 to less than about 100 mTorr. whereupon the microwave source 26 is energized to ignite a plasma, generally at a RF energy level of about 0.08 to 1.6 KW, as understood by one skilled in the art. During pressure reduction, methanol vapor is introduced by line 48 from the storage vessel 52 to maintain and achieve a minimum concentration of at least about 95 volume percent. Since oxygen is a known corrosive agent for some metallic instruments, it is desirable to achieve as high as possible concentration level of methanol vapor on the sterilization chamber 20 prior to plasma ignition.

Plasma generation is maintained for a time sufficient to reach an acceptable end point of sterilization, such as from 1 to about 60 minutes as a function of total energy. Generally, the microwave source 26 is operated to generate an electromagnetic field power density of from 0.01 Watts/cm$^3$ to about 0.2 Watts/cm$^3$ for a time sufficient to provide a total energy input of at least about 150 KJoules. Preferably, the radiated energy of the electromagnetic field is at a frequency of from about $10^5$ to $10^{15}$ Hertz. The electromagnetic field may be pulsed and/or half or full wave rectified or of a low ripple three phase source. In this context the tray 22 width and length are sized so as not to be evenly divisible by one-fourth of the wave length of the RF source.

After sufficient energy has been delivered to the sterilization assembly 10, the RF energy source 26 and the vacuum pump 58 are discontinued and the vessel 18 is vented to atmosphere via conduits 54 and 60 under the control of valve 62.

It will be understood by one skilled in the art that heat may be generated during the process of the present invention, and as such effects the rate of microbicidal results. Should heat be generated, it is desired not to permit elevated temperature levels above about 160° to 170° C. In the event temperatures should reach about 160° to 170° C., the control panel 28 modulates the RF energy source 26 to maintain such temperature level.

Figure 2:
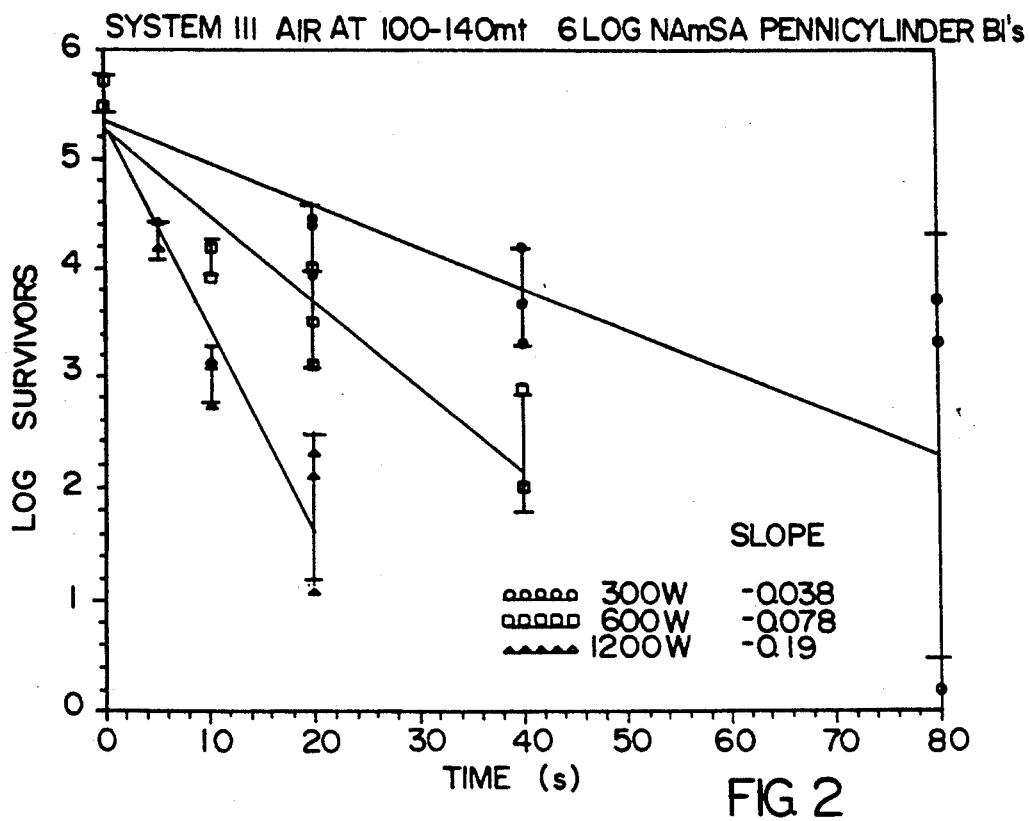
FIG. 2 is a graph illustrating kill rate as a function of power in the Kill versus Time relationship.
Figure 3:
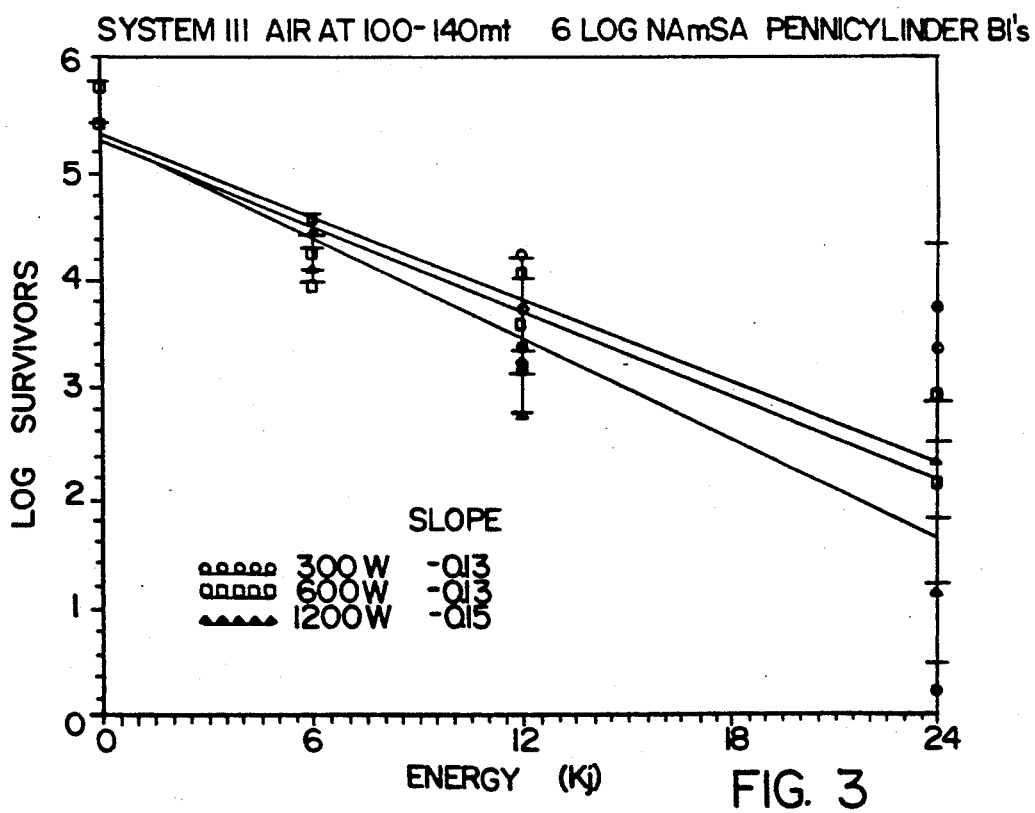
FIG. 3 is a graph of the same date as FIG. 2, normalized to total applied energy, illustrating constant energy effects in Kill vs. Energy relationship.
Figure 4:
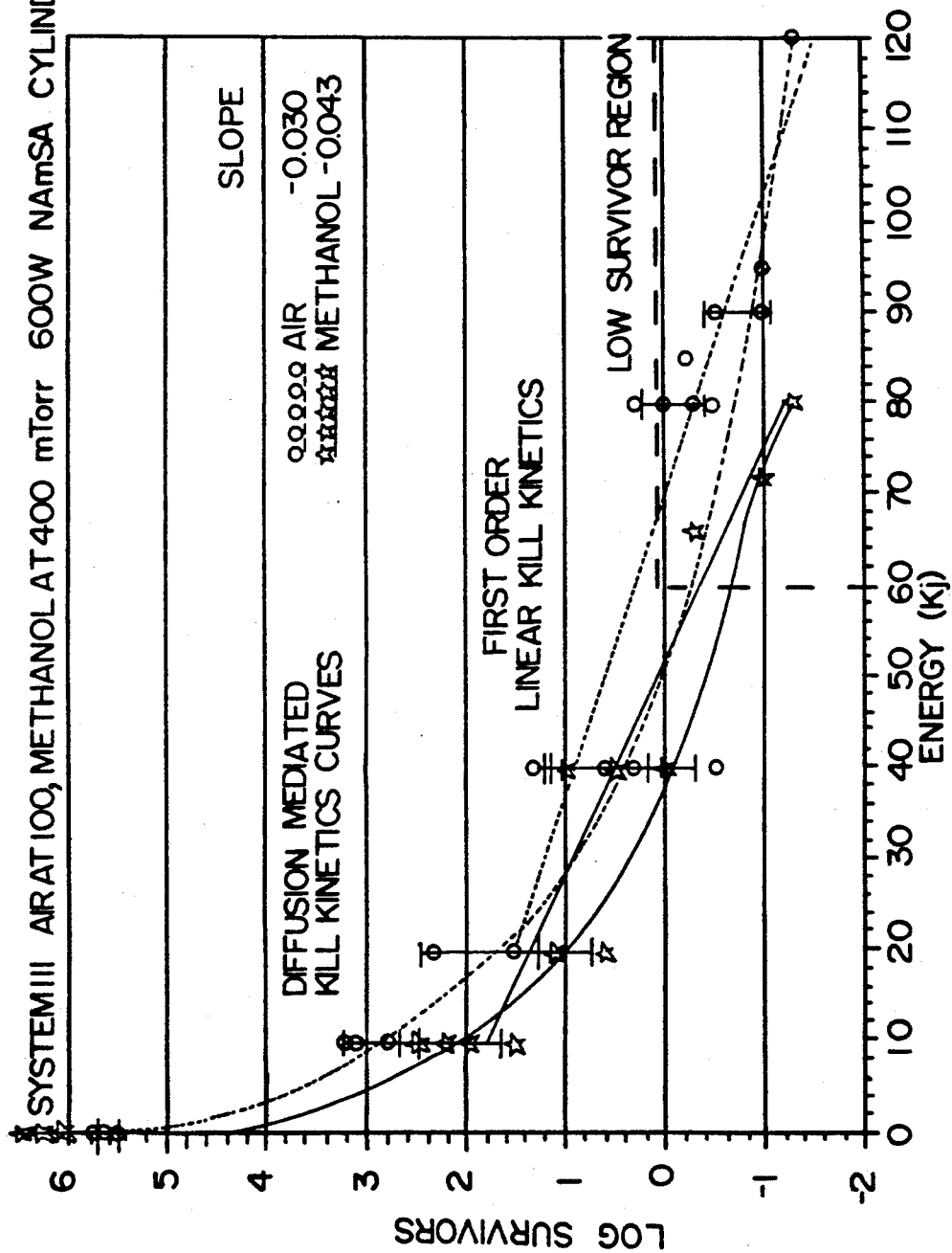
FIG. 4 is a graph comparing the Kill kinetics of air and methanol plasmas illustrating superiority of methanol plasma sterilization in Kill vs. Energy relationship.

Operation of the process of the present invention is illustrated in the graphs of FIGS. 2, 3 and 4. It is evident that effectiveness or kill is time dependent as a function of power level. Thus, the curves of FIG. 2 illustrate the characteristic doubling of slope as the power is doubled. Variance between the 80 sec. 300 w samples is believed due to non-homogenity of plasma at low powers in large sterilization chambers.

In FIG. 3, the curves essentially illustrate a constant kill rate at constant energy input regardless of the rate of applied energy over two doubling of rate. Thus, kill or totallity of microbicidal effect is proportional to the total energy applied to the system provided adequate time for the diffusion process.

As readily understood by one skilled in the art, effective sterilization is the totality of destruction or strong microbicidal effect to zero survival, although as a practical matter, an impossible state to validate absolutely. The FDA has provided a guideline for a testing protocol for determining microbicidal effectiveness referencing a shape of a survivor curve, a minimum contact time and a D value determined from experimental results of both quantitative kill kinetics and fraction positive/-negative probability of sterilization analyses. Thus, spericial activity, as recommended by the FDA, is a sterilizing process reliable to assure a probability of survival of less than one organism out of 1,000,000 or alternately less than $1 \times 10^{-6}$. In FIG. 4, these analyses are illustrated for air and methanol plasma processes.

While the microbicidal mechanism is not completely understood, it is believed that extremely potent microbicidal agents in micromolar concentrations are synthesized from the aliphatic alcohol, particularly from methanol. With the alcohol there is obviated the need to stock and handle bulk quantities of dangerous chemical sterilants, e.g. ethylene oxide, formaldehyde, etc. Additionally, the alcohols and particularly methanol may be conveniently used in the precleaning/drying process as a solvent. The use of substantially pure methanol compared with the $C_2+$ aliphatic alcolhols is preferred since undesired polymerization products may be formed with the heavier alcohols and be deposited on the instruments being sterilized. While processing conditions may be used which minimize such polymerization conditions, process control may be unduly complicated compared with the simplicity of using methanol.

It is understood by one skilled in the art that methanol may be admixed with water, hydrogen peroxide, and/or other of the low molecular weight organic compounds although the use of substantially pure methanol is preferred. Since hydrogen is believed to be generated during plasma generation, the presence of minor amounts of oxygen scavenges hydrogen thereby increasing the yields of micromolar concentrations of the potent microbicidal agents. Thus, the addition of minor quantities of less than about 0.3 m of an oxygen containing material during plasma generation may enhance the sterilization process of the present invention.

The process of the present invention is clean, rapid and energy efficient compared with the existing chemical, heat, etc. technologies. Methanol, the preferred low molecular weight aliphatic alcohol is not corrosive to articles being sterilized as well as being safer to the operators and the environment. Still further, while the process of the present invention is described with the generation of a plasma within the sterilization chamber about the article being sterilized, plasma generation may be effected in another microwave assembly and passed to the sterilization chamber of the present invention.

While the invention has been described in connection with an exemplary embodiment thereof, it will be understood that many modifications will be apparent to those of ordinary skill in the art; and that this application is intended to cover any adaptations of variations thereof. Therefore, it is manifestly intended that this invention be only limited by the claims and the equivalents thereof.

What is claimed is:

1. A plasma sterilization assembly, which comprises:
   a microwave means defining a microwave chamber;
   means for generating RF energy within said microwave chamber;
   a sterilization vessel defining a sterilization chamber disposed inside said microwave chamber;
   perforated tray means disposed in said sterilization chamber for receiving an article to be sterilized;
   a storage vessel containing a low molecular weight aliphatic alcohol;
   vacuum pump for evacuating said sterilization chamber;
   conduit means providing fluid flow communication between said sterilization chamber and said vacuum pump;
   conduit means for introducing vaporous low molecular weight aliphatic alcohol into said sterilization chamber from said storage vessel; and
   means for energizing said means for generating said RF energy to a level to form a plasma of said low molecular weight aliphatic alcohol and thereby generate micro-molecular concentrations of microbicidal agents.

2. The plasma sterilization assembly as defined in claim 1 wherein said means for generating RF frequency is in the range of from $10^5$ to $10^{15}$ Hertz. wherein a source of RF energy is between 0.08 to 1.6 KW.

3. The plasma sterilization assembly as defined in claim 1 or 2 wherein said means for generating is capable of generating RF energy between 0.8 to 1.6 KW.

4. The plasma sterilization assembly as defined in claim 1 wherein said vacuum pump maintains a vacuum of from 10 mTorr to 10 Torr.

5. The plasma sterilization assembly as defined in claim 1 and further including means to modulate said means for generating RF frequency to maintain a temperature in said sterilization chamber below about 160° C. to 170° C.

6. The plasma sterilization assembly as defined in claim 1 wherein said perforated tray is sized to be not evenly divisible by one-fourth of the wave length of an RF source.

7. The plasma sterilization assembly as defined in claim 1 and further including cooling means in fluid communication with said microwave chamber.

8. The plasma sterilization assembly as defined in claim 1 and further including an electrically conductive shield disposed on said perforated tray means.

* * * * *